United States Patent [19]
Frye
[11] 4,387,176
[45] Jun. 7, 1983

[54] SILICONE FLAME RETARDANTS FOR PLASTICS

[75] Inventor: Robert B. Frye, Albany, N.Y.

[73] Assignee: General Electric Company, Waterford, N.Y.

[21] Appl. No.: 345,941

[22] Filed: Feb. 4, 1982

[51] Int. Cl.$^3$ ...................... B32B 25/20; C08L 83/04; D02G 3/00

[52] U.S. Cl. ...................................... 524/268; 106/18; 106/18.11; 106/18.12; 106/18.26; 252/609; 260/DIG. 24; 428/375; 428/391; 428/921; 524/395; 524/400; 524/425; 524/434; 524/437; 524/451; 524/506; 524/588

[58] Field of Search .................... 106/18, 18.12, 18.11, 106/18.26; 252/609; 524/400, 588, 268, 395, 506; 523/179; 260/DIG. 24; 428/375, 391, 921

[56] References Cited

U.S. PATENT DOCUMENTS

| | | | |
|---|---|---|---|
| 2,744,079 | 5/1956 | Kilbourne et al. | 524/268 |
| 3,505,276 | 4/1970 | Hutchinson | 524/588 |
| 3,929,704 | 12/1975 | Horning | 524/268 |
| 3,983,082 | 9/1976 | Pratt et al. | 523/179 |
| 4,257,932 | 3/1981 | Beers | 524/588 |
| 4,320,044 | 3/1982 | Nakamura | 524/588 |

*Primary Examiner*—Ronald W. Griffin
*Attorney, Agent, or Firm*—Michael J. Doyle; Gary L. Loser; John L. Young

[57] ABSTRACT

There is provided flame retardant thermoplastic compositions and masterbatch formulations effective for rendering thermoplastics flame retardant. A typical flame retardant composition could be comprised of 50 to 97 percent by weight of thermoplastic, 1 to 40 percent of a silicone base such as a linear silicone fluid or gum, 1 to 20 percent of a metal organic compound such as magnesium stearate, and 1 to 20 percent of a silicone resin such as MQ resin which is soluble in the silicone base.

89 Claims, No Drawings

SILICONE FLAME RETARDANTS FOR PLASTICS

FIELD OF THE INVENTION

The present invention relates to flame retardant compositions and particularly flame retardant thermoplastics such as polyolefins and others. The invention is also directed to additives and particularly silicone-based additive compositions which offer flame retardant properties for plastics.

BACKGROUND OF THE INVENTION

There have been numerous attempts in the prior art to provide flame retardant thermoplastics. Typically it has been necessary to heavily fill the plastic or thermoplastic material with additives until the desired degree of flame retardancy had been achieved. However, this offered several disadvantages insofar as a large proportion of additives could normally be expected to detract from the physical properties of the plastic base. Furthermore, it was not unusual to find in a single system large quantities of halogen-containing materials as well as metal compounds.

It will be seen that the present invention provides improved flame retardant compounds which not only require a lower relative proportion of additives, but also avoid the necessity for utilizing organic halides and certain metal compounds such as antimony oxide, which may be undesirable in certain applications.

In U.S. Pat. No. 4,235,978 (Luce et al.) there is disclosed a flame retardant composition comprised of an admixture of a thermoplastic polymer, a flame retardant additive which is either a low molecular weight polymer of a carbonate of a halogenated dihydric phenol, or a combination of such carbonate compounds and an inorganic or organic antimony-containing compound and up to about 5 weight percent of a diorganopolysiloxane gum.

In U.S. Pat. No. 4,209,566 (Betts et al.) there is disclosed a method of enhancing the electrical properties of polymeric electrical insulation which contain a polar halogen compound by treating the polar halogen compound with a heat reactive liquid silicone polymer which is then heated and reacted throughout the halogen compound.

In U.S. Pat. No. 4,247,446 (Betts et al.) there is disclosed a flame resistant composition comprised of a crosslinked polyolefin, decabromodiphenyl ether, silicone gum and dibasic lead phthalate.

In U.S. Pat. No. 4,273,691 (MacLaury et al.) there is disclosed a flame resistant composition comprised of a blend of organic polymer, silicone polymer and a Group IIA metal carboxylate salt containing six to twenty carbon atoms. Copending patent application Ser. No. 344,167 filed Jan. 29, 1982 (Frye et al.), discloses flame retardant compositions which utilize a different range of silicone polymers, namely low viscosity silanol and trimethyl silyl chainstopped polysiloxane fluids.

In U.S. Pat. No. 4,265,801 (Moody et al.) there is disclosed a flame retarded, melt processable polymer composition which is comprised of a blend of non-silicone polymer such as a thermoplastic, a solid, non-elastomeric, mono-organic polysiloxane resin (a so-called MT resin) and a filler.

All of the foregoing patents and applications are hereby incorporated by reference. It will become apparent that the present inventor has herein provided novel flame retardant compositions which exhibit significant improvements over the prior art compositions.

The present invention is based upon the discovery that efficient flame retardant plastics can be provided by combining in the correct proportions certain metal soaps (e.g. magnesium stearate) with a mixture of certain silicone resins such as a polytriorganosilyl silicate and a polydiorganosiloxane polymer. For example, adding this combination to a polypropylene homopolymer can enable it to exhibit properties meeting the requirements of the well known Underwriter's Laboratories UL-94 vertical burn test. Furthermore, exceptional flame retardancy can be achieved in certain compositions of the present invention without the use of a halogen or antimony oxide; and certain optimized formulations utilizing the compositions of the present invention will enable those skilled in the art to achieve superior V-0 rated plastics when relatively small amounts of certain halogen-containing compounds are also utilized.

This invention differs from the prior art in several respects, notably in that it requires the use of a combination of polyorganosiloxane silicone and a silicone resin, thereby achieving a synergistic flame retardant effect which is not taught by the prior art. The degree of flame retardancy is significantly greater and it was quite surprising that improved flame retardancy could be achieved by the addition of certain specified amounts of silicone resin in combination with previously known flame retardant compositions such as those described by MacLaury et al. or Frye et al.

The metal/silicone/silicone resin flame retardant of the present invention provides at least three significant advantages over the commonly used halogen/antimony oxide systems for thermoplastics: (1) the metal/-silicone/silicone resin system is free from the acidic and perhaps toxic by-products released by halogen and antimony upon burning, (2) the typical concentration of the metal/silicone/silicone resin additive composition needed for a V-1 type flammability formulation is in the range of 20% and hence the mechanical properties of a flame retarded thermoplastic containing the additive composition are not altered to as great a degree as the same thermoplastic in which other flame retardant additives have been incorporated in higher concentrations to obtain equivalent flame retardant properties, and (3) the presence of silicone provides an improvement in the processability of the polymer, thereby adding an unexpected beneficial side effect. Additionally, thermoplastic products containing the flame retardant additives of the present invention when prepared according to the process of the present invention exhibit a higher level of gloss than finished thermoplastic products containing conventional flame retardant additives. In addition, the relatively low amount of metal/silicon silicone resin necessary for good flame retardance permit typical flame retardant formulations of the present invention to be less expensive than conventional flame retardant formulations based on the same polymer system. Polypropylene, for example, is a large volume thermoplastic having many desirable properties such as solvent and moisture resistance but also having high flammability. The invention herein described can provide a desirable V-1 grade of flame retardant polypropylene using only about 20% total flame retardant additives by weight and omitting antimony oxide and halogen. By contrast, commercially available flame retardant grades of polypropylene use 30–50% by weight of organic halide and an antimony oxide synergist ($Sb_2O_3$). These high additive loadings increase the cost of the formulation and decrease its tensile strength and other physical properties. The increase in cost and change in properties make commercial flame retardant polypropylene unsuitable for many applications. Additionally, the presence of antimony oxide in such compositions raises concerns about (1) toxicity and carcinogenicity, (2) char afterglow, and (3) product appearance. Further $Sb_2O_3$ can cause a brightening effect which will require the use of additional pigment in applications with critical appearance specifications.

In the present invention antimony oxide has been replaced by silicone, a silicone resin such as an MQ resin, and a metal salt such as an alkaline-earth metal carboxylate additive such as magnesium stearate. These additives are non-toxic, do not support char afterglow, can be used at lower levels, and may contribute to other beneficial properties such as processability, lubricity, mold release, and gloss. The smaller proportion of flame retardant additives required in this invention is expected to have less of a detrimental effect on the physical properties of the thermoplastic than do the heavier loadings of commercial formulations. Furthermore, it is expected that the improved physical properties will in turn facilitate expanded uses for flame retarded thermoplastics.

It is therefore an object of the present invention to provide improved flame retardant additives for plastics which utilize a novel combination of silicone and silicone resin and metal soap, but which do not require the use of either organic halide or antimony oxide.

There are also provided flame retarded thermoplastic compositions and articles made therefrom which contain a combination of silicone, silicone resin and metal soap.

There are also provided processes for achieving each of the aforesaid objectives.

These and other objects will become apparent to those skilled in the art upon consideration of the present specification and claims.

DESCRIPTION OF THE INVENTION

The present invnetion provides an additive formulation or masterbatch formulation capable of improving the flame retardant properties of thermoplastics. The invention is also directed to novel flame retardant thermoplastic compositions and processes for providing the same.

An additive package or masterbatch formulation is a composition which is generally comprised of a mixture of the following ingredients:

i. 40 to 80 percent by weight of silicone;

ii. 5 to 40 percent by weight of a Group IIA metal organic compound; and, iii. 2 to 40 percent by weight of a silicone resin which is soluble in the aforementioned silicone (i.) and which is effective for imparting improved flame retardant character to plastics.

Such a flame retardant additive composition may be further comprised of a compatibilizing amount of a thermoplastic which is effective for facilitating the dispersion of such a masterbatch formulation or additive package in a specific thermoplastic which is to be rendered flame retardant by the addition of the additive package of the present invention. Thus it will be recognized that ease of handling, storage, manufacture and use can be facilitated by incorporating such thermoplastics into the flame retardant additive package. Additive packages or masterbatches for plastics are well known in the art and are often known as additive concentrates.

The flame retardant additive composition of the present invention can thereafter be incorporated into a thermoplastic to be rendered relatively flame retardant by any suitable means which will provide a homogeneous dispersion of the additive in the thermoplastic (i.e. twin screw extrusion, etc.).

The first major ingredient contained in the flame retardant additive formulation is approximately 40 to 80 percent by weight of silicone. The term "silicone" as used herein is generic for a wide range of polysiloxane materials which can be advantageously utilized in the composition of the present invention. For purposes of the present specification it is intended that the expression "silicone" be construed as including those effective silicone materials as described by MacLaury and Holub in U.S. Pat. No. 4,273,691, as well as those materials described by Frye and Torkelson in copending patent application Ser. No. 344,167 filed Jan. 29, 1982, as well as other effective silicone materials, several of which will be described below. Typically effective silicone materials will be those silicone fluids or gums which are organopolysiloxane polymers comprised of chemically combined siloxy units typically selected from the group consisting of $R_3SiO_{0.5}$, $R_2SiO$, $R^1SiO_{1.5}$, $R^1R_2SiO_{0.5}$, $RR^1SiO$, $(R^1)_2SiO$, $R SiO_{1.5}$ and $SiO_2$ units and mixtures thereof wherein each R represents independently a saturated or unsaturated monovalent hydrocarbon radical, $R^1$ represents a radical such as R or a radical selected from the group consisting of a hydrogen atom, hydroxyl, alkoxy, aryl, vinyl, or allyl radicals etc. and wherein said organopolysiloxane has a viscosity of approximately 600 to 300,000,000 centipoise at 25° C. A preferred silicone material is a polydimethylsiloxane having a viscosity of approximately 90,000 to 150,000 centipoise at 25° C. Such effective silicone materials will be collectively referred to as either silicones or silicone oils and are to be distinguished from the class of materials referred to as silicone resins. Such silicone oils are readily available under a wide variety of brand and grade designations.

The second ingredient of the masterbatch formulation or flame retardant additive package is a Group IIA metal organic compound or salt. Group IIA metal carboxylic acid salts containing at least six carbon atoms as discussed by MacLaury et al. are particularly effective, and a notable example of a preferred metal compound is magnesium stearate. However, it is believed that other Group IIA metals such as calcium, barium, and strontium will also provide effective frame retardant additive compositions.

Among the contemplated carboxylic acids from which salts of the Group IIA alkaline-earth metals can be derived, it is believed that approximately at least six carbon atoms are required to effectively disperse the Group IIA metal in the silicone base, and in turn to assure that the Group IIA metal is fully dispersed in the thermoplastic to be rendered flame retardant. It is contemplated that little advantage would be found by utilizing carboxylic acid salts containing more than about 20 carbon atoms, although salts may well be useful in specific applications. It is to be noted that it is not presently felt that finely divided Group IIA metal per se would be an effective ingredient in the flame retardant additive compositions of the present invention. However, it may be possible that such effective Group IIA metal additives could be effectively complexed with other organic moieties, and therefore find effective use in such compositions by virtue of their ability to readily disperse throughout the silicone base. It is therefore intended that the Group IIA metal salt represent not only those effective Group IIA metal carboxylic acid salts as described, but also such other organic complexes of such metals as are effective for use in such flame retardant applications. Metal salts of other materials may be equally effective. Salts of the following acids may be suitable: sulfinic, sulfonic, aromatic sulfenic, sulfamic, phosphinic and phosphoric acids. Included within the Group IIA metal carboxylic acid salts which can be utilized in the practice of the present invention are, for example, magnesium stearate, calcium stearate, barium stearate, strontium stearate. The carboxylic acid salts include: stearates (including isostearates), oleates, palmitates, myristates, laurates, undecylenates, 2-ethylhexanoates, hexanoates, etc.

The remaining major ingredient of the materbatch composition or flame retardant additive package formulation is a class of materials referred to as silicone resin. The present inventor has discovered that remarkably effective flame retardant thermoplastic compositions can be provided when one or more of such a silicone resin is combined with the previously described ingredients to provide a flame retardant additive composition. Silicone resins are well known materials coming in a variety of forms. Approximately 2 to 40 precent by weight of the total additive formulation will be a silicone resin which is soluble in the above described silicone oil (i.e. fluid or gum) and which is effective for imparting improved flame retardancy to the compositions of the present invention. Among the preferred silicone resins are MQ silicone resins. The expression "MQ silicone resin" refers to the fact that such resins are typically comprised primarily of monofunctional M units of the formula $R_3SiO_{0.5}$ and tetrafunctional Q units of the average formula $SiO_2$ having a specified ratio of M to Q units. A notable effective silicone resin for use in the present invention is polytrimethylsilylsilicate which can have a ratio of, approximately, 0.3 to 4.0 M units per Q unit. A particularly effective masterbatch formulation might preferably contain from 6 to 30 percent by weight of such MQ resin and have a ratio of, approximately, 0.6 to 2 M units per Q units. An example of a commercially available MQ silicone resin in General Electric SR545 (60% MQ resin solids in toluene). A preferred method of utilizing such an MQ resin solution is to mix it with the silicone oil component and thereafter remove the solvent. The solvent can be removed by well known methods, e.g. by distillation at moderate temperatures.

It is contemplated that other silicone oil soluble forms of solid silicone resins may be effective for use in the flame retardant compositions of the present invention. Indeed, MT and TQ silicone resins (where T represents trifunctional $RSiO_{1.5}$ units) may also be effective as well as mixtures and copolymers of each of the resins mentioned. These silicone resins are well known materials and are readily available. A criteria for suitability is that such effective silicone resinous materials be soluble or dispersible in the silicone oil base.

Additionally it is to be noted that although the additive composition specifies the silicone oil (essentially D functional) and silicone resin (M, D, T, or Q functional) as discrete ingredients to be admixed, it is intended that the present invention encompass reaction products of such materials which may be equally effective as flame retardant additives. It is also foreseeable that a copolymer containing requisite M, D, T or Q functionality may be utilized in place of discrete silicone oil and silicone resin constituents.

Naturally the masterbatch composition or flame retardant additive package can contain additional optional ingredients, such as, approximately, 5 to 40 percent by weight of the masterbatch composition of an organic halide. A typical thermoplastic composition of the present invention could contain 1 to 20 percent by weight of organic halide. An example of such an organic halide is decabromodiphenyl oxide. Another is Dechlorane Plus, a chlorinated alicyclic hydrocarbon available from Hooker Chemical Corporation. Another effective yet optional ingredient would be, approximately, 5 to 80 percent by weight of the total thermoplastic composition of aluminum trihydrate. Those skilled in the art of compounding will recognize the temperature constraints of aluminum trihydrate.

Although it is one of the objects of the present invention to avoid the use of antimony metal yet provide satisfactory thermoplastic compositions, it is contemplated that certain thermoplastic formulations designed to meet specific property requirements may nonetheless contain approximately 1 to 10 percent by weight of antimony oxide as an additional optional ingredient should it be so desired.

Therefore the masterbatch composition may optionally contain approximately 5 to 20 percent by weight of antimony oxide, based upon the weight of the masterbatch formulation.

Additionally such masterbatch formulations may contain various fillers selected from the group consisting of, for example, talc, clay, Wollastonite, calcium carbonate, additional aluminum trihydrate, etc. It is contemplated that excessive amounts of such fillers could have deleterious effects on flame retardancy and individual formulations can be optimized for particular filler loadings.

The spirit and scope of the present invention also encompass novel flame retardant thermoplastic compositions which typically can be thermoplastics combined with the above described masterbatch formulations or can be admixtures of the discrete ingredients. Such a flame retardant composition would therefore be comprised of:

a. 50 to 97 percent by weight of thermoplastic;
b. 1 to 40 percent by weight of silicone;
c. 1 to 20 percent by weight of Group IIA metal organic salt containing 6 or more carbon atoms; and,
d. 1 to 20 percent by weight of silicone resin soluble in silicone (b.) and which is effective for imparting improved flame retardant character to the thermoplastic. Among the particularly preferred silicone resins, as mentioned above, is an MQ silicone resin comprised of monofunctional M units of the formula $R_3SiO_{0.5}$ and tetrafunctional Q units of the formula $SiO_2$ having an average ratio of approximately 0.3 to 4.0 M units per Q unit.

Included among the organic polymers which can be used to make the flame retardant compositions of the present invention or to which the flame retardant additives of the present invention may be added are, for example, polyolefins such as: polyethylenes such as low density polyethylene (LDPE) and high density polyethylene (HDPE); polypropylene, polybutylene, etc. and copolymers of these; lpolystyrene, polycarbonate such as LEXAN$^R$ brand and thermoplastic polyesters such as VALOX$^R$ resin, both manufactured by the General Electric Company, and other polymers such as polyamides (e.g. Nylon 66, Nylon 12 etc.), polycaprolactams, ionomers, polyurethanes, co- and ter-polymers of acrylonitrile, butadiene and styrene; as well as acrylic polymers, acetal resin, ethylene-vinyl acetate, polymethylpentene, flexible polyvinylchloride, polyphenylene oxide, polyphenylene oxide-polystyrene blends or copolymers such as NORYL$^R$ polymer (manufactured by General Electric); Monsanto Santoprene and Uniroyal TPR thermoplastic polyesters. Those skilled in the art will now be able to adapt and optimize the flame retardant compositions of the present invention to a wide variety of thermoplastic formulations including engineering plastics. It is not intended that the above listing be all inclusive, and the present invention should not be so limited.

In addition, heat activated peroxides can be optionally used for those thermoplastics which may conventionally utilize such materials. Suitable reactive peroxides are disclosed in U.S. Pat. Nos. 2,888,424, 3,086,966 and 3,214,422. Such peroxide crosslinking agents include organic tertiary peroxides which decompose at a temperature above about 295° F. and thereby provide free-radicals. The organic peroxides can be used in amounts of from about 2 to 8 parts by weight of peroxide per 100 parts of organic polymer. A preferred peroxide is dicumyl peroxide, while other peroxides such as VulCupR$^R$ of Hercules, Inc., a mixture of para and meta a,a',-bis(t-butylperoxy)-diisopropylbenzene, etc., can be used. Curing coagents such as triallyl cyanurate can be employed in amounts of up to about 5 parts by weight of coagent, per 100 parts of the polymer if desired. The polyolefins can be irradiated by high energy electrons, x-ray and like sources as necessary. Additionally it may be desirable to provide a catalyst effective for crosslinking or curing the silicone components of the compositions of the present invention.

In the practice of the present invention, the flame retardant compositions can be made by mixing together the organic polymer with the silicone oil and silicone resin and the Group IIA metal organic salt, hereinafter referred to as the "Group IIA salt" by means of any conventional compounding or blending apparatus, such as a Banbury mixer or on a 2-roll rubber mill. Order of addition of the particular constituents does not appear to be critical; and, those skilled in the art will be able to optimize the flame retardant compositions contemplated herein without undue experimentation.

A preferred method of providing the flame retardant thermoplastic compositions of the present invention is to premix the silicone component with the MQ resin solution, and thereafter remove the solvent as by distillation, thereby ensuring complete dispersion of the resin in the oil. This solution is thereafter combined with the remaining ingredients by any suitable means for providing a homogeneous composition (e.g. twin screw extrusion).

Preferably all the ingredients are formulated together except those which are sensitive to the temperatures in the range of from about 300° F. to about 400° F., such as heat decomposable peroxides. The ingredients are therefore at a temperature sufficient to soften and plasticize the particular organic polymer if feasible. An effective procedure, for example, would be to uniformly blend the aforementioned ingredients at a suitable temperature in the absence of the optional organic peroxide, then introduce the organic peroxide (if it is necessary ) at a lower temperature to uniformly incorporate it into the mixture.

The proportions of the various ingredients can vary widely depending upon the particular application intended. For example, effective flame retardance can be achieved within the ranges of materials discussed above. However, greater or smaller amounts may suffice in particular applications. Reinforcing and non-reinforcing fillers also may be employed such as those mentioned above for inclusion in the masterbatch formulations. Flame retardant thermoplastics can contain such fillers in an amount of, approximately, 5 to 70 percent by weight of the total composition.

The flame retardant composition of the present invention can be extruded onto a conductor such as copper wire and the like, and in particular instances it can be crosslinked depending on whether organic peroxide curing agent is present. Of course, there are numerous other applications where the flame retardant compositions of the present invention may be used to great advantage. Such flame retardant thermoplastic materials may be successfully molded, extruded, spun or compressed, etc. to form numerous useful products such as moldings, sheets, webbing, fibers and a multitude of other flame retardant thermoplastic products. Thus, the flame retardant compositions of the present invention also can be utilized in such applications as appliance housings, hairdryers, television cabinets, smoke detectors, automotive interiors, fans, motors, electrical components, coffee makers, pump housings, power tools, etc. Such flame retardant compositions might also be utilized in fabrics, textiles and carpet as well as many other applications.

Those skilled in the art will appreciate that there are several methods for testing and comparing relative flame retardancy of thermoplastics. Among the most well known are limiting oxygen index, horizontal burn times (HBT) and vertical burn times (VBT). Underwriters' Laboratories, Inc. Bulletin UL-94 describes a "Burning Test for Classifying Materials" (hereinafter referred to as UL-94).

In accordance with this test procedure, materials so investigated are rated either UL-94 V-O, UL-94 V-I, or UL-94 V-II based on the results of five specimens. The criteria for each V rating per UL-94 is briefly as follows: "UL-94 V-O": average flaming and/or glowing after removal of the igniting flame shall not exceed 5 seconds and none of the specimens shall drip particles which ignite absorbent cotton. "UL-94 V-I": average flaming and/or glowing after removal of the igniting flame shall not exceed 25 seconds and none of the specimens shall drip particles which ignite absorbent cotton. "UL-94 V-II": average flaming and/or glowing after removal of the igniting flame shall not exceed 25 seconds and the specimens drip flaming particles which ignite absorbent cotton.

The vertical burn tests conducted in connection with the following examples essentially follow the test procedures described in UL-94. However, the tests, since they were designed for screening purposes only and not for qualification of the products for specific applications, were not replicated to the extent set forth in the procedure. Therefore reference to UL-94 V-O, V-I, and V-II formulations in the teaching of the present invention in the examples represents the inventor's characterization of the flame retardant formulations which he believes will produce articles meeting the pertinent test criteria of UL-94.

In order that those skilled in the art will be better able to practice the invention, the following examples are given by way of illustration and not by way of limitation. All parts are by weight unless otherwise specified.

EXAMPLE 1

A mixture of 149.7 parts by weight of a silanol stopped polydimethylsiloxane polymer having a nominal viscosity of 90,000–150,000 centipoise (90–150 Pascal sec.) and 104 parts by weight of magnesium distearate were compounded together on a 2-roll mill to make a white paste. 42.4 g of this paste was then compounded into 295 g of molten polypropylene (Hercules Pro-Fax 6523) using an oil heated 2-roll mill at approximately 390° F. Following the paste addition, 27.2 g of decabromodiphenyl oxide (Great Lakes DE-83R) and 12.9 g of polytrimethylsilyl silicate were also compounded into the polypropylene. This MQ resin has an M to Q ratio of approximately 0.8 to 1 and was prepared by oven drying the resin solution sold by General Electric as SR-545. The compounding was repeated until approximately 5 pounds of product were obtained. This material was then granulated to a convenient size for injection molding.

For comparison, both an unmodified Pro-Fax 6523 polypropylene sample and a commercial flame retarded grade of polypropylene containing organic halide (U.S.S. Novamont Moplen CRV08) were also injection molded. Although some delamination was seen in the molding compositions containing the silicone based flame retardant additives of the present invention, it is notable that the mechanical properties were generally better than the commercial flame retardant grade as seen in Table 1. The delamination was probably due to a combination of incomplete mixing and molding conditions, and this problem can be overcome by proper compounding in, for example, an extruder. Subsequent examples do not typically show this effect.

TABLE 1

| Tests on Injection Molded Samples | Unmodified Pro-Fax 6523 Polypropylene | Pro-Fax 6523 Plus the Silicone Flame Retardant Pkg | USS Novamont CRV08 V-0 Grade Polypropylene |
|---|---|---|---|
| Appearance | Hazy transparent | Glossy white | Dull off-white |
| Vertical Burn (UL-94) | Flaming drips consumed 5"/ 146 sec. | Extinguishes in 25 sec. NO DRIP | Extinguishes in 1 sec. No drips |
| Tensile Strength at Yield (ASTM D638) | 4800 psi | 3500 psi | 2700 psi |
| Tensile Strength at Break | 2900 psi | 3100 psi* | 2500 psi |
| Elongation at Break | 357% | Approximately 293%** | 55% |
| Notched Izod Impact (ASTM D246A) | 0.609 ft-lb/in | 1.116 ft-lb/in | 0.463 ft-lb/in |
| Heat Distortion Temp. (264 psi) (ASTM D648) | 57.5–66° C. | 60–62° C. | 62–69° C. |
| 260 h QUV Exposure*** | Yellow | White; some chalking | Tan |
| Limiting Oxygen Index (ASTM D2863-77) | 17.4 | 28.5 | 23.9 |

Notes for Table 1:
*Value is affected by the energy of delamination
**Average of 3 values after dropping the highest and lowest
***Cycle is 8h of UV at 60° C. and 4h of condensation at 50° C.

EXAMPLE 2

The following ingredients were weighed and compounded into polypropylene (Hercules Pro-Fax 6523) on a 380° F. 2-roll mill, in each case the polydimethylsiloxane and magnesium stearate were premixed on a room temperature mill to form a white paste. The polydimethylsiloxane, the decabromodiphenyl oxide, and the MQ resin used were the same as those described in Example 1.

TABLE 2

| Formulation | Pro-Fax 6523 | Silicone | Magnesium Stearate | Decabromo-Diphenyl Oxide | Other |
|---|---|---|---|---|---|
| A | 156.4 g | 13.2 g | 9.2 g | 14.4 g | 6.8 g MQ resin |
| B | 149.6 g | 13.2 g | 9.2 g | 14.4 g | None |
| C | 156.4 g | 20.0 g | 9.2 g | 14.4 g | None |
| D | 156.4 g | 13.2 g | 9.2 g | 14.4 g | 6.8 g MS-7[(1)] |
| E | 156.4 g | 13.2 g | 9.2 g | 14.4 g | 6.8 g treated MS-7[(2)] |

Notes for Table 2:
[(1)]Cab-O-Sil MS-7 fumed silica from Cabot Corporation
[(2)]Cab-O-Sil MS-7 fumed silica with silicone surface treatment These five formulations were compression molded at approximately 375° F. in a picture frame mold to form a $\frac{1}{8}'' \times 6'' \times 6''$ slab. A duplicate of formulation A was prepared and granulated before compression molding; this was called formulation F. The slabs were cut into $\frac{1}{8}'' \times \frac{1}{2}'' \times 6''$ strips for flammability tests. Vertical burn tests were run similarly to the Underwriters Laboratories Test UL-94 method discussed above; the results are shown in Table 3.

TABLE 3

| Formulation | VERTICAL BURN TEST: 10 Sec. Ignition | VERTICAL BURN TEST: 10 Sec. Re-Ignition | Limiting Oxygen Index |
|---|---|---|---|
| A | Extinguished in 11 sec.; no drips | Extinguished in 20 sec.; no drips | 27.8 |
| B | Extinguished in 28 sec.; flaming drips | Extinguished in 28 sec.; flame fell off | 35.0 |
| C | Extinguished in 31 sec.; flaming drips | Extinguished in 38 sec.; flaming drip | 32.7 |
| D | Extinguished in 40 sec.; no drips | Extinguished in 26 sec.; flame fell off | 31.2 |
| E | Extinguished in 58 sec.; no drips | Extinguished in 63 sec.; flaming drip | 31.7 |

TABLE 3-continued

| Formulation | VERTICAL BURN TEST 10 Sec. Ignition | 10 Sec. Re-Ignition | Limiting Oxygen Index |
|---|---|---|---|
| F | Extinguished in 12 sec.; no drips | Extinguished in 5 sec.; no drip | — |

These results indicate the surprising finding that the presence of MQ resin in combination with silicone and magnesium stearate will enhance the self-extinguishment and inhibit dripping in the vertical burn test for flame retarded thermoplastics. Fumed silica (Q-functional material) or silicone treated fumed silica (DQ-functional material) do not appear to produce the same effect as MQ resin. As is typical, the oxygen index test does not correlate well with vertical burn tests in these formulations, because each test measures different properties.

EXAMPLE 3

Formulations described in Table 4 were compounded, molded, and tested as in Example 2, and test results are indicated in Table 5.

TABLE 4

| Formulation | Pro-Fax 6523 | Silicone | MQ Resin | Magnesium Stearate | Decabromo-Diphenyl Oxide | Other |
|---|---|---|---|---|---|---|
| A | 156.4 g | 13.2 g | 6.8 g | 9.2 g | 14.4 g | None |
| B | 156.4 g | 13.2 g | — | 9.2 g | 14.4 g | 6.8 g SR-350(1) |
| C | 156.4 g | 13.2 g | — | 9.2 g | 14.4 g | 6.8 g SR-355(2) |
| D | 156.4 g | 13.2 g | — | 9.2 g | 14.4 g | 20 g silicone/MQ(3) |
| E | 156.4 g | 13.2 g | — | 9.2 g | 14.4 g | 20 g vinylsilicone/vinyl MQ(4) |
| F | 156.4 g | 13.2 g | 2.4 g | 9.2 g | 14.4 g | 17.6 g vinylsilicone/vinyl MQ(4) |

Notes for Table 4:
(1)A silicone binder resin sold by General Electric
(2)A silicone binder resin sold by General Electric
(3)A .9–1.7 Pascal sec. material resulting from stripping the solvent from a mixture of 86 parts silanol stopped polydimethylsiloxane (nominal viscosity .6–.9 Pascal sec.) and 23.3 parts of 60% MQ resin in xylene solution.
(4)A 60–75 Pascal sec. material prepared by stripping the solvent from a mixture of vinyl stopped polydimethylsiloxane (nominal viscosity 50–90 Pascal sec.) and a vinyl containing MQ resin.

TABLE 5

| Formulation | 10 Sec. Ignition | 10 Sec. Re-Ignition |
|---|---|---|
| A | Extinguished in 15 sec.; no drips | Extinguished in 5 sec.; no drips |
| B | Extinguished in 16 sec.; no drips | Extinguished in 55 sec.; flaming drips |
| C | Extinguished in 18 sec.; no drips | Extinguished in 87 sec.; flaming drips |
| D | Extinguished in 8 sec.; no drips | Extinguished in 7 sec.; no drips |
| E | Extinguished in 17 sec.; 2 flaming drips | Extinguished in 58 sec.; flaming drips |
| F | Extinguished in 16 sec.; no drips | Extinguished in 18 sec.; flame fell off |

Further testing of formulation D showed it had a limiting oxygen index of 26.8 and self-extinguished in a horizontal burning test with no dripping in 3 sec. to 16 sec.

These results demonstrate that the binder resins (which are relatively high in methyl T content) appear to be less efficient than MQ resin in the flame retardant formulation. Also, combining the silicone and MQ resin solution and then removing the solvent gives a flame retardant additive which works as well or better than MQ resin which is dried before incorporation into the silicone.

EXAMPLE 4

The formulations described in Table 6 were compounded in a 380° F. 2-roll mill, granulated, and compression molded as in Example 2. Strips were cut from the molded slabs and subjected to the UL-94 vertical burn test. Test results are reported in Table 7.

TABLE 6

| Formulation | Pro-Fax 6523 | Silicone | MQ Resin | Magnesium Stearate | Decabromo-Diphenyl Oxide | Other |
|---|---|---|---|---|---|---|
| A | 156.4 g | 13.2 g | 6.8 | 9.2 g | 14.4 g | None |
| B | 156.4 g | 13.2 g | 6.8 | 9.2 g | — | 14.4 g Dechlcrane plus (Hooker) |
| C | 156.4 g | — | — | 9.2 g | 14.4 g | 20 g silicone-MQ(1) |
| D | 156.4 g | — | 4.7 | 9.2 g | 14.4 g | 15.4 g silicone-MQ(1) |
| E | 156.4 g | — | — | 9.2 g | 14.4 g | 20 g silicone-MQ(2) |
| F | 156.4 g | — | — | 9.2 g | 14.4 g | 20 g silicone MQ(3) |
| G | 156.4 g | — | — | 9.2 g | 14.4 g | 20 g silicone-MQ(4) |

Notes for Table 6:
(1)The residue after removing the solvent from a mixture of 86 parts silanol-stopped polydimethylsiloxane (.6–.9 Pascal sec.) and 23.3 parts 60% MQ resin in xylene.
(2)A mixture of 277.2 g MQ resin solution (60% solids in toluene) and 322.8 g silanol-stopped polydimethylsiloxane (nominal viscosity of 2.5–3.5 Pascal sec.) with solvent removed.
(3)Same as in Note 2, but using a silicone with viscosity of 15–30 Pascal sec.
(4)A mixture of 277.2 g MQ resin solution (60% solids in toluene) and 322.8 g silanol-stopped polydimethylsiloxane (nominal viscosity of 90–150 Pascal sec.) with solvent removed.

TABLE 7

| Formulation | 10 Sec. Ignition | 10 Sec. Re-Ignition |
|---|---|---|
| A | Extinguished in 11 sec.; no drips | Extinguished in 13 sec.; no drips |
| B | Extinguished in 125 sec.; one flaming drip | Extinguished in 91 sec.; flaming drips |
| C | Extinguished in 20 sec.; no drips | Extinguished in 3 sec.; no drips |
| D | Extinguished in 11 sec.; no drips | Extinguished in 11 sec.; no drips |
| E | Extinguished in 10 sec.; no drips | Extinguished in 9 sec.; no drips |
| F | Extinguished in 8 sec.; no drips | Extinguished in 3 sec.; no drips |
| G | Extinguished in 8 sec.; no drips | Extinguished in 8 sec.; no drips |

The results described in Table 7 demonstrate that silicones of several viscosities when premixed with MQ resin solution and subsequently stripped of solvent perform well in the flame retardant formulations.

EXAMPLE 5

An investigation of the effectiveness of the silicone flame retardant formulation of the present invention was undertaken for polyethylene. The additives were compounded int Union Carbide's DYNH1 grade of low density polyethylene using the 380° F. 2-roll mill. A $\frac{1}{8}'' \times \frac{1}{2} \times 6''$ strip from a compression molded slab of the formulation and a strip of the unmodified DYNH1 were compared. 156.4 g of DYNH1 was compounded with 13.2 g silicone having a nominal viscosity of 90,000 to 150,000 cps, 6.8 g dry MQ resin, 9.2 g magnesium stearate and 14.4 g decabromodiphenyl oxide. In the UL-94 vertical burn test, the unmodified DYNH1 polyethylene was consumed in 17 seconds with flaming drips. The modified polyethylene, however, self-extinguished in 20 seconds with no drips after a 10 second ignition, and after a 10 second reignition the sample extinguished in 37 seconds, although this time with some flaming drips. Although the formulation has not been optimized for low density polyethylene, flame retardance is evident.

EXAMPLE 6

Evaluation of the silicone flame retardant package was conducted for an impact grade of polystyrene. The formulation was compounded on the hot mill, granulated, and compression molded. 156.4 g of impact polystyrene (American Hoechst Fosta-Tufflex 9100/721MI) was combined with 13.2 g silicone having a nominal viscosity of 90,000 to 150,000 cps, 2.3 g dry MQ resin, 13.2 g magnesium stearate, 0.1 g antimony trioxide and 16.6 g decabromodiphenyl oxide. In the UL-94 vertical burn test an unmodified sample of the polystyrene was consumed, however the modified version self-extinguished in 7 seconds with no drips after the first 10 second ignition, and it also self-extinguished in 3 seconds with no drips after the 10 second reignition. The example is indicative of flame retardance in polystyrene, and it is believed that further optimization of the formulation by those skilled in the art will remove the need for antimony.

EXAMPLE 7

The silicone flame retardant additive composition was also evaluated in other thermoplastics of present commercial interest. These formulations were not optimized but rather were used in the same proportions as in one of the better polypropylene compositions. Nonetheless, a measure of flame retardance is indicated. Thus a masterbatch of silicone flame retardant was prepared by mixing together on a 2-roll mill at ambient temperature, 20 parts of the stripped silanol/MQ solution (see Note #4 in Example 4), 9.2 parts of magnesium stearate, and 14.4 parts of decabromodiphenyl oxide. Then on the heated 2-roll mill 43.6 g of the masterbatch was compounded with 156.4 g of each of the four thermoplastics: polycarbonate, polystyrene, styrene-acrylonitrile polymer, and acrylonitrile-butadiene-styrene copolymer. These compositions as well as control resins were compression molded into 6"×6"×$\frac{1}{8}$" sheets and then cut to 6"×178 "×$\frac{1}{8}$" for the vertical burn, horizontal burn and oxygen index tests.

The test data displayed in Table 7 demonstrate that the silicone flame retardant optimized for polypropylene will also exert a significant flame retarding effect on other thermoplastics such as polycarbonate, crystalline polystyrene, SAN and ABS. In the Table the abreviation SFR represents the flame retarding masterbatch formulation which is combined with the specified thermoplastic.

TABLE 8

| Thermoplastic | Horizontal Burn[1] | Vertical Burn[2] | Oxygen Index |
|---|---|---|---|
| Polycarbonate (Lexan®) | SE 1 s/SE 1 sec. | SE 30 s ND/SE 3 s FD | 23 |
| Polycarbonate + SFR | SE 1 s/SE 1 sec. | SE 3 s ND/SE 12 s ND | 26 |
| Polystyrene (Cosden 525 P-1) | Consumed, 2"/180 s, FD | — | 18 |
| Polystyrene + SFR | SE 13 s ND/SE 8 s ND | SE 28 s ND/SE 30 s ND | 26 |
| SAN (Monsanto Lustran SAN 31) | Consumed, 2"/160 s, FD | — | 18 |
| SAN + SFR | SE 21 s ND/SE 17 s ND | SE 12 s ND/SE 18 s ND | 26 |
| ABS (Borg-Warner DFA-1000R) | Consumed | — | 18 |
| FR-ABS (Borg-Warner KJB-1000) | SE 1 s/SE 1 s | SE 1 s/SE 1 s | 30 |
| ABS + SFR | SE 32 s ND/SE 18 s ND | SE 13 s ND/SE 20 s ND | 26 |

Notes for Table 8:
[1]A 6" × ½" × ⅛" strip was held in the horizontal position, ignited, and the rate of burning was measured; this was repeated on the other end.
[2]A 6" × ½" × ⅛" strip was held vertically, the lower end was ignited by holding in a Bunsen burner flame for 10 seconds and then the time for self-extinguishment was measured; when burning ceased the piece was immediately reignited for another 10 seconds.
Note:
SE = self-extinguishes
ND = no drips
FD = flaming drips
s = seconds

EXAMPLE 8

A mixture of 78.2 parts of Pro-Fax 6523 polypropylene homopolymer, 8.5 parts of the solvent-free silicone oil-MQ resin (as in Note #4 of Example 4), 2.7 parts magnesium stearate, and 10.6 parts decabromodiphenyl oxide were compounded in a twin screw extruder. A strand was extruded which was approximately 75 mils in diameter. A strand sample was held in a horizontal position, ignited for 5 seconds with a Bunsen burner flame, and observed. It self-extinguished in 1–15 seconds after each of six consecutive ignitions. In three of the ignitions no flaming drips were observed; in the other three ignitions the flame fell off as a drip. Holding the strand in a vertical position and igniting the lower end gave similar results. A control sample, extruded Pro-Fax 6523, burned vigorously with many flaming drips.

EXAMPLE 9

On a hot (370° F.) 2-roll mill were compounded together 78.2 g polypropylene (heat stabilized homopolymer Hercules Pro-Fax 6523), 6.6 g silanol stopped polydimethylsiloxane of nominal viscosity of 90,000–150,000 centipoise available from General Electric Company, 3.4 g polytrimethylsilyl silicate (dried MQ resin), 4.6 g magnesium stearate, and 7.2 g decabromodiphenyl ether. The resulting mass was compression molded at approximately 375° F. to form a ⅛"×6"×6" slab and then cut into test strips of ⅛"×½"×6". In the UL-94 vertical burn test these strips self-extinguished in 6–21 seconds with no flaming drips. The strips had a limiting oxygen index value of 29 and self-extinguished in a horizontal burning test in 3–4 seconds without dripping. The UL-94 performance of these samples meets the requirements for a V-1 classification.

EXAMPLE 10

On a 2-roll hot mill (approximately 400° F.) were compounded 165.9 g polypropylene homopolymer (Hercules Pro-Fax 6523), 24.8 g of the silicone mix prepared as in Note #4 of Example 4 and 9.3 g of magnesium stearate. The resulting mass was compression molded at approximately 375° F. in a picture frame mold to form a ⅛"×6"×6" slab. Two ⅛"×½"×6" strips were cut from this slab and subjected to the UL-94 type vertical burn test. The first strip self-extinguished with no dripping in 10 seconds after a 10 second ignition using a Bunsen flame and after immediate reignition the strip self-extinguished with no dripping in 26 seconds. The second strip gave extinguishing times of 9 and 66 seconds.

EXAMPLE 11

A series of formulations were prepared using the same procedure as described in Example 10. In some formulations a common talc filler (Cyprus Mistron Vapor 139) was also included. The quantities of inputs are shown in Table 9 and the results from the vertical burn test are shown in Table 10. The most promising formulations appear to be B, C, D, G, and N. Although these five each use more than 10% silicone by weight, the total additive weights are 25% or less of the polypropylene and yet they produce V-1 performance, in the absence of either halogen or antimony.

TABLE 9

| | FORMULATION | | |
|---|---|---|---|
| Silicone* | Magnesium Stearate | Mistron 139 Talc | Pro-Fax 6523 |
| A 24.8 g | 9.3 g | 0 g | 165.9 g |
| B 27.3 g | 10.2 g | 0 g | 162.5 g |

TABLE 9-continued

| | FORMULATION | | |
|---|---|---|---|
| Silicone* | Magnesium Stearate | Mistron 139 Talc | Pro-Fax 6523 |
| C 22.3 g | 8.4 g | 20.0 g | 149.3 g |
| D 21.4 g | 7.1 g | 14.3 g | 157.1 g |
| E 10.7 g | 3.6 g | 21.4 g | 164.3 g |
| F 21.4 g | 3.6 g | 21.4 g | 153.6 g |
| G 23.1 g | 3.8 g | 7.7 g | 165.4 g |
| H 11.5 g | 11.5 g | 23.1 g | 153.8 g |
| I 12.5 g | 12.5 g | 8.3 g | 166.7 g |
| J 25.0 g | 12.5 g | 8.3 g | 154.2 g |
| K 15.8 g | 7.9 g | 15.8 g | 160.5 g |
| L 34.4 g | 13.5 g | 0 | 152.1 g |
| M 31.1 g | 2.8 g | 0 | 166.0 g |
| N 39.1 g | 6.5 g | 0 | 154.3 g |

*As prepared in Example 4, Note #4.

TABLE 10

| | VERTICAL BURN | | | |
|---|---|---|---|---|
| | Strip #1 | | Strip #2 | |
| Formulation | Ignite | Re-Ignite | Ignite | Re-Ignite |
| A | 26 s SE/ND | 6 s SE/ND | 12 s SE/ND | 23 s SE/ND |
| B | 7 s SE/ND | 2 s SE/ND | 6 s SE/ND | 12 s SE/ND |
| C | 6 s SE/ND | 1 s SE/ND | 11 s SE/ND | 17 s SE/ND |
| D | 6 s SE/ND | 9 s SE/ND | 4 s SE/ND | 10 s SE/ND |
| E | 24 s SE/ND | Consumed | 32 s SE/ND | Consumed |
| F | 9 s SE/ND | 14 s SE/ND | 8 s SE/ND | 51 s SE/ND |
| G | 25 s SE/ND | 6 s SE/ND | 8 s SE/ND | 9 s SE/ND |
| H | 110 s SE/ND | 28 s SE/ND | 18 s SE/ND | 106 s SE/ND |
| I | 35 s SE/ND | 5 s SE/ND | 11 s SE/ND | 42 s SE/ND |
| J | 3 s SE/ND | 51 s SE/ND | 5 s SE/ND | 40 s SE/ND |
| K | 14 s SE/ND | 47 s SE/ND | 39 s SE/ND | 40 s SE/ND |
| L | 6 s SE/ND | 2 s SE/ND | 17 s SE/ND | 33 s SE/ND |
| M | 20 s SE/ND | 21 s SE/ND | 36 s SE/ND | 10 s SE/ND |
| N | 7s SE/ND | 5 s SE/ND | 16 s SE/ND | 4 s SE/ND |

Notes for Table 10:
s = seconds
SE = self-extinguish
ND = no drips
FD = drips which ignite surgical cotton

EXAMPLE 12

A masterbatch of the metal/silicone/halogen flame retardant was prepared by milling together at ambient temperature 20 parts by weight of the silicone solution prepared as in Note #4 of Example 4 above, 9.2 parts by weight of magnesium stearate, and 14.4 parts by weight of decabromodiphenyl oxide (DE-83R Great Lakes Chemical). The resulting mixture was a white pasty substance. Four formulations described in Table 11 were prepared using this masterbatch, polypropylene (Pro-Fax 6523), and aluminum trihydrate (Solem SB-632). They were compounded on a 400° F. 2-roll mill by first banding the polypropylene and then adding the masterbatch followed by the aluminum trihydrate. The resulting mass was granulated and then compression molded into ⅛"×6"×6" slabs using a Pasadena press and a picture frame mold at 375° F. Flammability bars (⅛"×½"×6") were cut from the slab and evaluated using a vertical burn test (UL-94). The results in Table 12 show that adding aluminum trihydrate at 20% by weight (Formulation B) improves the flame retardance from V-1 to V-0. Higher loadings of aluminum trihydrate do not appear to be as advantageous. The oxygen index of B was 25%.

TABLE 11

| Formulation | Masterbatch | Aluminum Trihydrate | Polypropylene |
|---|---|---|---|
| A | 43.6 g | — | 156.4 g |

TABLE 11-continued

| Formulation | Masterbatch | Aluminum Trihydrate | Polypropylene |
|---|---|---|---|
| B | 34.9 g | 40 g | 125.1 g |
| C | 32.7 g | 50 g | 117.3 g |
| D | 30.5 g | 0 g | 109.5 g |
| E | 28.3 g | 70 g | 101.7 g |

TABLE 12

| Vertical Burn Results Formulation | | |
|---|---|---|
| A, Strip 1 | 14 sec SE-ND/2 sec SE-ND | V-1 |
| Strip 2 | 8 sec SE-ND/2 sec SE-ND | V-1 |
| B, Strip 1 | 5 sec SE-ND/2 sec SE-ND | V-0 |
| Strip 2 | 4 sec SE-ND/3 sec SE-ND | V-0 |
| Strip 3 | 5 sec SE-ND/1 sec SE-ND | V-0 |
| Strip 4 | 7 sec SE-ND/2 sec SE-ND | V-0 |
| C, Strip 1 | 2 sec SE-ND/10 sec SE-ND | V-1 |
| Strip 2 | 26 sec SE-ND/21 sec SE-ND | V-1 |
| Strip 3 | 4 sec SE-ND/2 sec SE-ND | V-1 |
| Strip 4 | 12 sec SE-ND/4 sec SE-ND | V-1 |
| D, Strip 1 | 12 sec SE-ND/10 sec SE-ND | V-1 |
| Strip 2 | 10 sec SE-ND/11 sec SE-ND | V-1 |
| E, Strip 1 | 5 sec SE-ND/22 sec SE-ND | — |
| Strip 2 | 13 sec SE-ND/33 sec SE-ND | — |

Notes for Table 12:
SE = self-extinguish
ND = no flaming drips

EXAMPLE 13

Another formulation was made identically to those in Example 12 except that only 10% aluminum trihydrate was used. Thus 20 g of aluminum trihydrate, 39 g of masterbatch, and 140.8 g of the polypropylene were compounded, granulated, and molded and tested. In the vertical burning test, strip 1 self-extinguished in 8 seconds with no drips, and upon reignition it also self-extinguished with no drips. The second strip gave the same results in 8 and 4 seconds, respectively. Thus a 10% level of aluminum trihydrate can provide a V-1 formulation, but a 20% level appears to be more effective.

EXAMPLE 14

A test was conducted to determine if aluminum trihydrate would be effective in the absence of halogen, and a non-halogen containing V-1 formulation was used. This formulation consisted of 123 g polypropylene, 31 g of the silicone solution (from Note #4 of Example 4), and 5 g of magnesium stearate. To this was added 40 g of aluminum trihydrate (i.e. 20% by weight of the total formulation). After compounding, granulating, and compression molding, the vertical burn test was run. Each strip self-extinguished with no drips after each of two ignitions. Strip 1 required 13 and 43 seconds respectively, and strip 2 required 21 and 28 seconds respectively. It appears that aluminum trihydrate did not improve the non-halogen containing V-1 formulation.

EXAMPLE 15

The 10 formulations shown in Table 13 were prepared and evaluated as in Example 12. Each formulation contains the selected filler at 20% by weight. The results demonstrate that aluminum trihydrate improves the flame retardance of the system. It appears that high levels of other fillers such as talc and fumed silica can be deleterious while treated $CaCO_3$ and Wollastonite have little effect on flammability in the formulation of this example.

TABLE 13

| Formulation | Master Batch | Polypro-Pylene | Filler |
|---|---|---|---|
| A | 34.9 g | 125.1 g | 40 g talc (Mistron 139, Cyprus) |
| B | 34.9 g | 125.1 g | 40 g treated talc (Cyprabond, Cyprus) |
| C | 34.9 g | 125.1 g | 40 g fumed silica (Cabosil MS-7) |
| D | 34.9 g | 125.1 g | 40 g silane treated silica |
| E | 34.9 g | 125.1 g | 40 g aluminum trihydrate (Solem SB-632) |
| F | 34.9 g | 125.1 g | 40 g treated aluminum trihydrate (Solem SB-632 SA) |
| G | 34.9 g | 125.1 g | 40 g stearate treated $CaCo_3$ (OMYA BSH) |
| H | 34.9 g | 125.1 g | 40 g Wollastonite (NYAD 400) |

Although V-0 performance was not achieved in this particular experiment (perhaps due to processing variables), nevertheless the formulations containing aluminum trihydrate showed the best flame retardance, as seen in Table 14.

TABLE 14

| Formulation | 10-Sec Ignition/Re-ignition |
|---|---|
| A-1 | 16 sec SE-ND/22 sec SE-ND |
| A-2 | 7 sec SE-ND/14 sec SE-ND |
| B-1 | 127 sec consumed, FD |
| B-2 | 102 sec SE-ND/31 sec SE-FD |
| C-1 | 162 sec consumed, FD |
| C-2 | 129 sec consumed, FD |
| D-1 | 181 sec consumed, FD |
| D-2 | 159 sec consumed, FD |
| E-1 | 8 sec SE-ND/6 sec SE-ND |
| E-2 | 10 sec SE-ND/10 sec SE-ND |
| F-1 | 6 sec SE-ND/8 sec SE-ND |
| F-2 | 8 sec SE-ND/19 sec SE-ND |
| G-1 | 15 sec SE-ND/24 sec SE-ND |
| G-2 | 16 sec SE-ND/57 sec SE-ND |
| H-1 | 14 sec SE-ND/9 sec SE-ND |
| H-2 | 8 sec SE-ND/6 sec SE/ND |

Notes for Table 14:
SE = self-extinguish
ND = no flaming drip
FD = flaming drips (ignites cotton)

EXAMPLE 16

A phenyl silicone gum (13.8 mole percent diphenyl siloxane) appears to work well in the flame retardant formulation of the present invention when incorporated in polypropylene, polystyrene and polycarbonate. To a 1-liter kettle were added 277.2 g MQ resin (60% solution of MQ resin in xylene; a polytrimethylsilyl silicate with a nominal ratio of 0.8 of M to Q species) and 322.8 g of a 13.8 mole percent diphenyl polydimethylsiloxane gum (silanol stopped, with a penetration of 300–700). The ingredients were agitated and slowly heated to 140° C. under reduced pressure (10–30 Torr) to strip off the xylene. The resulting resinous product was compounded on a 2-roll mill at 380°–400° F. with magnesium stearate (MgSt), decabromodiphenyl oxide (DBDPO), and a thermoplastic. The material was granulated, compression molded, and tested. The formulations were comprised of the following ingredients and the results of the vertical burn test are shown in Table 15:

| | Silicone | MgSt | DBDPO | Plastic |
|---|---|---|---|---|
| (1) | 19 g | 8.7 g | 13.7 g | 148.6 g Polypropylene (Pro-Fax 6523) |
| (2) | 19 g | 8.7 g | 13.7 g | 148.6 g Polystyrene (Cosden 525-P1) |

-continued

| | Silicone | MgSt | DBDPO | | Plastic |
|---|---|---|---|---|---|
| (3) | 19 g | 8.7 g | 13.7 g | 148.6 g | Polycarbonate (Lexan ®) |

TABLE 15

| VERTICAL BURN TEST | | |
|---|---|---|
| | 10-Sec Ignition | 10-Sec Re-Ignition |
| (1) | 3 sec SE, ND | 18 s SE, ND |
| | 2 sec SE, ND | 3 s SE, ND |
| (2) | 4 sec SE, ND | 12 s SE, ND |
| | 8 sec SE, ND | 34 s SE, ND |
| (3) | 3 sec SE, ND | 4 s SE, ND |
| | 2 sec SE, ND | 5 s SE, ND |

Notes for Table 15:
SE = self-extinguishing
ND = no dripping

EXAMPLE 17

Previous examples have utilized a ratio of approximately 2 parts silicone polymer per part MQ resin. It appears that equivalent flame retardance can also be obtained with reduced levels of MQ resin. This can be important since MQ resin is generally more expensive than the silicone polymer. A mixture of 46.2 parts of MQ resin (60% solution of MQ resin in toluene; a polytrimethylsilyl silicate with a nominal ratio of 0.8 of M to Q species) and 53.8 parts silicone (a silanol-stopped polydimethylsiloxane of nominal viscosity of 90,000–150,000 centipoise) was stripped of solvent by distillation of 140° C. in vacuo (approximately 20 Torr). The resulting resinous material had a viscosity of approximately 300,000 centipoise and contained an approximate ratio of 2:1 silanol polymer to MQ resin. This stock material was blended with various amounts of additional silicone to reduce the MQ level. These blends were compounded on a 2-roll mill with magnesium stearate and polypropylene at approximately 380° F. After granulating, the material was compression molded and cut into $\frac{1}{8}''\times\frac{1}{2}''\times 6''$ flammability bars and tested by the vertical burn test (similar to UL-94). The formulations are shown in Table 16. The results in Table 17 indicate that Vi performance can be achieved with reduced amounts of MQ resin.

TABLE 16

| Formulations | Silicone/MQ | Silicone | MgSt | Polypropylene | Comment |
|---|---|---|---|---|---|
| (1) | 39.2 g | — | 6.6 g | 154.5 g | Control |
| (2) | 35.2 g | 4 g | 6.6 g | 154.5 g | 10% less MQ |
| (3) | 31.3 g | 7.9 g | 6.6 g | 154.5 g | 20% less MQ |
| (4) | 27.4 g | 11.8 g | 6.6 g | 154.5 g | 30% less MQ |

TABLE 16-continued

| Formulations | Silicone/MQ | Silicone | MgSt | Polypropylene | Comment |
|---|---|---|---|---|---|
| (5) | 23.5 | 15.7 g | 6.6 g | 154.5 g | 40% less MQ |

TABLE 17

| | VERTICAL BURN TESTS | |
|---|---|---|
| Formulation | 10 Sec. Ignition | 10 Sec. Re-Ignition |
| 1 | 18s SE/ND | 24s SE/ND |
| | 8s SE/ND | 11s SE/ND |
| 2 | 8s SE/ND | 4s SE/ND |
| | 16s SE/ND | 3s SE/ND |
| 3 | 13s SE/ND | 17s SE/ND |
| | 23s SE/ND | 4s SE/ND |
| 4 | 11s SE/ND | 3s SE/ND |
| | 10s SE/ND | 3s SE/ND |
| 5 | 13s SE/ND | 5s SE/ND |
| | 17s SE/ND | 3s SE/ND |

Notes for Table 17:
SE = self extinguishing
ND = no drip

EXAMPLE 18

In order to evaluate what effect the flame retardant additives of the present invention may have on on the physical properties of flame retarded plastics, eleven formulations were premixed using a 2-roll mill and a Henschel mixer, and then extruded with a twin screw co-rotating extruder, and thereafter pelletized. The silicone additives of the present invention referred to in formulation B were comprised of approximately 38.8 parts silicone oil/MQ resin as described in Note #4 of Example 4, 12.4 parts magnesium stearate, and 48.8 parts decabromodiphenyl oxide.

Formulation (A)—Pro-Fax 6523 polypropylene
(B)—78.2 pts Pro-Fax+21.8 pts silicone additives
(C)—80 pts Pro-Fax+20 pts talc (Mistron 139)
(D)—80 pts (B)+20 pts talc
(E)—80 pts Novamont (CRVO8+20 pts talc
(F)—90 pts Pro-Fax+10 pts talc
(G)—90 pts (B)+10 pts talc
(H)—90 pts Novamont CRVO8+10 parts talc
(I)—80 pts Pro-Fax+20 pts calcium carbonate
(J)—80 pts (B)+20 pts calcium carbonate
(K)—100 pts Novamont CRVO8

The test data tabulated in Table 18 demonstrate that polypropylene (B) containing the additives of the present invention has a higher tensile strength, higher notched Izod impact resistance, higher melt flow, higher oxygen index, and higher channel flow than a commercial flame retarded polypropylene.

TABLE 18

| Formulation | Vertical Burn Test | Oxygen Index % | Melt Flow (g/10 min.) | HDT A 264 psi (°C.) | Notched Izod (ft-lb/in.) | Channel Flow (inches) | Tensile At Yield (psi) | Tensile At Break (psi) |
|---|---|---|---|---|---|---|---|---|
| A Pro-Fax 6523 (PP) | Consumed | 18 | 3.7 | 58 | .82 | 8.50 | 5400 | 3100 |
| B Silicone Addit. + PP | Marginal V-1 | 27 | 10.3 | 55 | .95 | 10.75 | 4000 | — |
| C 20% Talc + PP | Consumed | 18 | 2.9 | 68 | .76 | 6.50 | 5000 | 1800 |
| D 20% Talc + B | 11–52 sec, SE,ND | 30 | 7.4 | 56 | .25 | 8.50 | 3400 | 1700 |
| E 20% Talc + CRV08 | V-0 | 24 | 6.9 | 68 | .91 | 6.25 | 2800 | 2600 |
| F 10% Talc + PP | Consumed | 18 | 3.2 | 63 | .69 | 7.25 | 5200 | 1800 |
| G 10% Talc + B | V-1 | 27 | 8.7 | 55 | .99 | 9.25 | 3600 | 1100 |
| H 10% Talc + CRV08 | V-0 | 23 | 9.6 | 65 | .25 | 6.75 | 2700 | 2400 |
| I 20% $CaCO_3$ + PP | Consumed | 18 | 2.1 | 63 | .82 | 6.25 | 4500 | 2000 |
| J 20% $CaCO_3$ + B | Consumed | 24 | 8.3 | 54 | .98 | 8.25 | 3000 | 2300 |

TABLE 18-continued

| Formulation | Vertical Burn Test | Oxygen Index % | Melt Flow (g/10 min.) | HDT A 264 psi (°C.) | Notched Izod (ft-lb/in.) | Channel Flow (inches) | Tensile At Yield (psi) | Tensile At Break (psi) |
|---|---|---|---|---|---|---|---|---|
| K CRV08 | V-0 | 24 | — | 60 | .61 | — | 2700 | 2500 |

In addition, it is believed that optimized silicone flame retardant compositions may have better electrical properties (dielectric strength), higher Gardner impact resistance, and better processability (extrusion rate and power consumption) than flame retardant material containing conventional flame retardant additives.

What is claimed is:

1. A flame retardant composition comprised of:

a. 50 to 97 percent by weight of thermoplastic;

b. 1 to 40 percent by weight of silicone;

c. 1 to 20 percent by weight of Group IIA metal organic salt; and, d. 1 to 20 percent by weight of a silicone resin soluble in silicone (b.) and effective for imparting flame retardancy to said thermoplastic.

2. A composition as in claim 1 wherein said silicone resin is an MQ silicone resin comprised of monofunctional M units of the average formula $R_3SiO_{0.5}$ and tetrafunctional Q units of the average formula $SiO_2$, and having an average ratio of, approximately, 0.3 to 4.0 M units per Q unit.

3. A composition as in claim 1 wherein said thermoplastic is selected from the group consisting of polypropylene, polyethylene, polycarbonate, polystyrene, acrylonitrile-butadiene-styrene terpolymer, polyphenylene oxide-polystyrene blends, acrylic polymer, polyurethane and polyamides.

4. A composition as in claim 1 wherein said silicone is an organopolysiloxane comprised of chemically combined siloxy units selected from the group consisting of $R_3SiO_{0.5}$, $R_2SiO$, $RSiO_{1.5}$, $R^1R_2SiO_{0.5}$, $RR^1SiO$, $(R^1)_2SiO$, $R^1\,SiO_{1.5}$ and $SiO_2$ units and mixtures thereof wherein each R represents independently a saturated or unsaturated monovalent hydrocarbon radical, $R^1$ represents independently a saturated or unsaturated monovalent hydrocarbon radical or a radical selected from the group consisting of a hydrogen atom, hydroxyl, alkoxyl, aryl, vinyl, or allyl radicals and wherein said organopolysiloxane has a viscosity of approximately 600 to 300,000,000 centipoise at 25° C.

5. A composition as in claim 4 wherein said silicone is an essentially linear polydimethylsiloxane copolymer having a viscosity of 90,000 to 150,000 centipoise at 25° C.

6. A composition as in claim 1 wherein said Group IIA metal organic salt is a Group IIA metal carboxylic acid salt containing at least 6 carbon atoms.

7. A composition as in claim 6 wherein said Group IIA metal is selected from the group consisting of magnesium, calcium, barium and strontium.

8. A composition as in claim 6 wherein said carboxylic acid salt is selected from the group consisting of stearates, oleates, palmitates, myristates, laurates, undecylenates, 2-ethylhexanoates and hexanoates.

9. A composition as in claim 1 wherein said silicone resin is present in an amount of 1 to 10 percent by weight and is comprised essentially of polytrimethylsilyl silicate having a ratio of approximately 0.6 to 2 M units per Q unit.

10. A composition as in claim 1 further comprising approximately 1 to 20 percent by weight of the total composition of an organic halide.

11. A composition as in claim 10 wherein said organic halide is decabromodiphenyl oxide.

12. A composition as in claim 1 further comprising aluminum trihydrate in an amount of, approximately, 5 to 80 percent by weight of the total composition.

13. A composition as in claim 1 further comprising antimony oxide in an amount of, approximately, 1 to 10 percent by weight of the total composition.

14. A composition as in claim 1 further comprising a filler selected from the group consisting of talc, Wollastonite, and calcium carbonate.

15. A composition as in claim 1 further comprising an amount of catalyst effective for curing said composition thereby providing a flame retardant article.

16. A process for providing a flame retardant composition comprising the steps of: combining a. 50 to 97 percent by weight of thermoplastic;

b. 1 to 40 percent by weight of silicone;

c. 1 to 20 percent by weight of Group IIA metal organic salt; and, d. 1 to 20 percent by weight of a silicone resin soluble in said silicone (b.) and effective for imparting flame retardancy.

17. A process as in claim 16 wherein said silicone resin is an MQ silicone resin comprised of monofunctional M units of the average formula $R_3SiO_{0.5}$ and tetrafunctional Q units of the average formula $SiO_2$, and having an average ratio of, approximately, 0.3 to 4.0 M units per Q unit.

18. A process as in claim 16 wherein said thermoplastic is selected from the group consisting of polypropylene, polyethylene, polycarbonate, polystyrene, acrylonitrile-butadiene-styrene terpolymer, polyphenylene oxide-polystyrene blends, acrylic polymer, polyurethane and polyamides.

19. A process as in claim 16 wherein said silicone is an organopolysiloxane comprised of chemically combined siloxy units selected from the group consisting of $R_3SiO_{0.5}$, $R_2SiO$, $RSiO_{1.5}$, $R^1R_2SiO_{0.5}$, $(R^1)_2SiO$, $RR^1SiO$, $R^1SiO_{1.5}$ and $SiO_2$ units and mixtures thereof wherein each R represents independently a saturated and unsaturated monovalent hydrocarbon radical, $R^1$ represents independently a saturated or unsaturated monovalent hydrocarbon radical or a radical selected from the group consisting of a hydrogen atom, hydroxyl, alkoxyl, aryl, vinyl, or allyl radicals and wherein said organopolysiloxane has a viscosity of approximately 600 to 300,000,000 centipoise at 25° C.

20. A process as in claim 19 wherein said silicone is an essentially linear polydimethylsiloxane copolymer having a viscosity of 90,000 to 150,000 centipoise at 25° C.

21. A process as in claim 16 wherein said Group IIA metal organic salt is a Group IIA metal carboxylic acid salt containing at least 6 carbon atoms.

22. A process as in claim 16 wherein said Group IIA metal is selected from the group consisting of magnesium, calcium, barium and strontium.

23. A process as in claim 21 wherein said carboxylic acid salt is selected from the group consisting of stearates, oleates, palmitates, myristates, laurates, undecylenates, 2-ethylhexanoates and hexanoates.

24. A process as in claim 16 wherein said silicone resin is present in an amount of 1 to 10 percent by weight and is comprised essentially of polytrimethylsilyl silicate having a ratio of approximately 0.6 to 2 M units per Q unit.

25. A process as in claim 16 further comprising the step of adding, approximately, 1 to 20 percent by weight of the total composition of an organic halide.

26. A process as in claim 25 wherein said organic halide is decabromodiphenyl oxide.

27. A process as in claim 16 further comprising the step of adding aluminum trihydrate in an amount of, approximately, 5 to 80 percent by weight of the total composition.

28. A process as in claim 16 further comprising the step of adding antimony oxide in an amount of, approximately, 1 to 10 percent by weight of the total composition.

29. A process as in claim 16 further comprising the step of adding a filler selected from the group consisting of talc, Wollastonite, and calcium carbonate.

30. A process as in claim 16 further comprising the step of adding an amount of catalyst effective for curing said composition thereby providing a flame retardant article.

31. A process as in claim 16 further comprising the step of molding said flame retardant composition.

32. A process as in claim 16 further comprising the step of extruding said flame retardant composition.

33. A process as in claim 16 further comprising the step of spinning said flame retardant composition.

34. A process as in claims 31, 32, or 33 wherein said flame retardant composition is formed as a filament, fiber, film, web, fabric, sheet, molded part, extruded part, or spun part.

35. A process as in claim 16 further comprising the step of coating said flame retardant composition on a substrate.

36. A process as in claim 35 wherein said substrate is an electrical conductor.

37. A flame retardant article of manufacture comprised of a combination of:

a. 50 to 97 percent by weight of thermoplastic;
b. 1 to 40 percent by weight of silicone;
c. 1 to 20 percent by weight of Group IIA metal organic salt; and
d. 1 to 20 percent by weight of a silicone resin soluble in said silicone (b.) and effective for imparting flame retardancy to said article.

38. A flame retardant article as in claim 37 wherein said silicone resin is an MQ silicone resin comprised of monofunctional M units of the average formula $R_3SiO_{0.5}$ and tetrafunctional Q units of the average formula $SiO_2$, and having an average ratio of, approximately, 0.3 to 4.0 M units per Q unit.

39. A flame retardant article as in claim 37 wherein said thermoplastic is selected from the group consisting of polypropylene, polyethylene, polycarbonate, polystyrene, acrylonitrile-butadiene-styrene terpolymer, polyphenylene oxide-polystyrene blends, acrylic polymer, polyurethane and polyamide.

40. A flame retardant article as in claim 37 wherein said silicone is an organopolysiloxane comprised of chemically combined siloxy units selected from the group consisting of $R_3SiO_{0.5}$, $R_2SiO$, $RSiO_{1.5}$, $R^1R_2SiO_{0.5}$, $RR^1SiO$, $(R^1)_2SiO$, $R^1SiO_{1.5}$ and $SiO_2$ units and mixtures thereof wherein each R represents independently a saturated or unsaturated monovalent hydrocarbon radical, $R^1$ represents independently a saturated or unsaturated monovalent hydrocarbon radical or a radial selected from the group consisting of a hydrogen atom, hydroxyl, alkoxyl, aryl, vinyl, or allyl radicals and wherein said organopolysiloxane has a viscosity of approximately 600 to 300,000,000 centipoise at 25° C.

41. A flame retardant article as in claim 40 wherein said silicone is an essentially linear polydimethylsiloxane copolymer having a viscosity of 90,000 to 150,000 centipoise at 25° C.

42. A flame retardant article as in claim 37 wherein said Group IIA metal organic salt is a Group IIA metal carboxylic acid salt containing at least 6 carbon atoms.

43. A flame retardant article as in claim 37 wherein said Group IIA metal is selected from the group consisting of magnesium, calcium, barium and strontium.

44. A flame retardant article as in claim 37 wherein said carboxylic acid salt is magnesium stearate.

45. A flame retardant article as in claim 37 wherein said silicone resin is present in an amount of 1 to 10 percent by weight and is comprised essentially of polytrimethylsilyl silicate having a ratio of approximately 0.6 to 2 M units per Q unit.

46. A flame retardant article as in claim 37 further comprising approximately 1 to 20 percent by weight of the total flame retardant article of an organic halide.

47. A flame retardant article as in claim 46 wherein said organic halide is decabromodiphenyl oxide.

48. A flame retardant article as in claim 37 further comprising aluminum trihydrate in an amount of, approximately, 5 to 80 percent by weight of the total composition.

49. A flame retardant article as in claim 37 further comprising antimony oxide in an amount of, approximately, 1 to 10 percent by weight of the total composition.

50. A flame retardant article as in claim 37 further comprising a filler selected from the group consisting of talc, Wollastonite, and calcium carbonate.

51. A flame retardant article as in claim 37 further comprising an amount of catalyst effective for curing said composition thereby providing a flame retardant article.

52. A flame retardant article as in claim 37 wherein said formed part is molded.

53. A flame retardant article as in claim 37 wherein said formed part is extruded.

54. A flame retardant article as in claim 37 wherein said formed part is spun.

55. A flame retardant article as in claims 52, 53, or 54 wherein said formed part is a filament, fiber, film, web, fabric, sheet, molded part, extruded part or spun part.

56. A flame retardant article as in claim 37 wherein said formed part is a coating.

57. A flame retardant article as in claim 56 wherein said formed part is coated on an electrical conductor.

58. A composition effective for improving the flame retardant properties of thermoplastics comprising:

i. 40 to 80 percent by weight of silicone;
ii. 5 to 40 percent by weight of Group IIA metal organic salt; and,
iii. 2 to 40 percent by weight of a silicone resin soluble in said silicone (i.).

59. A composition as in claim 58 wherein said silicone resin is an MQ silicone resin comprised of monofunctional M units of the average formula $R_3SiO_{0.5}$ and tetra-functional Q units of the average formula $SiO_2$, and having an average ratio of, approximately, 0.3 to 4.0 M units per Q unit.

60. A composition as in claim 58 further comprising a compatiblizing amount of thermoplastic effective for facilitating the dispersion of said composition in a thermoplastic to be rendered flame retardant.

61. A composition as in claim 60 wherein said thermoplastic is selected from the group consisting of polypropylene, polyethylene, polycarbonate, polystyrene, acrylonitrile-butadiene-styrene terpolymer, polyphenylene oxide-polystyrene blends, acrylic polymer, polyurethane and polyamide.

62. A composition as in claim 58 wherein said silicone is an organopolysiloxane comprised of chemically combined siloxy units selected from the group consisting of $R_3SiO_{0.5}$, $R_2SiO$, $RSiO_{1.5}$, $R^1R_2SiO_{0.5}$, $RR^1SiO$, $(R^1)_2SiO$, $R^1SiO_{1.5}$ and $SiO_2$ units and mixtures thereof wherein each R represents independently a saturated or unsaturated monovalent hydrocarbon radical, $R^1$ represents independently a saturated or unsaturated monovalent hydrocarbon radical or a radical selected from the group consisting of a hydrogen atom, hydroxyl, alkoxyl, aryl, vinyl, or allyl radicals and wherein said organopolysiloxane has a viscosity of approximately 600 to 300,000,000 centipoise at 25° C.

63. A composition as in claim 62 wherein said silicone is an essentially linear polydimethylsiloxane copolymer having a viscosity of 90,000 to 150,000 at 25° C.

64. A composition as in claim 58 wherein said Group IIA metal organic salt is a Group IIA metal carboxylic acid salt containing at least 6 carbon atoms.

65. A composition as in claim 58 wherein said Group IIA metal is selected from the group consisting of magnesium, calcium, barium and strontium.

66. A composition as in claim 58 wherein said carboxylic acid salt is selected from the group consisting of stearates, oleates, palmitates, myristates, laurates, undecylenates, 2-ethylhexanoates and hexanoates.

67. A composition as in claim 58 wherein said silicone resin is present in an amount of 1 to 10 percent by weight and is comprised essentially of polytrimethylsilyl silicate having a ratio of approximately 0.6 to 2 M units per Q unit.

68. A composition as in claim 58 further comprising approximately 1 to 20 percent by weight of the total composition of an organic halide.

69. A composition as in claim 68 wherein said organic halide is decabromodiphenyl oxide.

70. A composition as in claim 58 further comprising aluminum trihydrate in an amount of, approximately, 5 to 80 percent by weight of the total composition.

71. A composition as in claim 58 further comprising antimony oxide in an amount of, approximately, 1 to 10 percent by weight of the total composition.

72. A composition as in claim 58 further comprising a filler selected from the group consisting of talc, wollastonite, and calcium carbonate.

73. A process for providing a composition effective for rendering thermoplastics flame retardant comprising the steps of combining:

i. 40 to 80 percent by weight of silicone;
ii. 5 to 40 percent by weight of Group IIA metal organic salt; and,
iii. 2 to 40 percent by weight of a silicone resin soluble in said silicone (i.).

74. A process as in claim 73 wherein said silicone resin is an MQ silicone resin comprised of monofunctional M units of the average formula $R_3SiO_{0.5}$ and tetrafunctional Q units of the average formula $SiO_2$, and having an average ratio of, approximately, 0.3 to 4.0 M units per Q unit.

75. A process as in claim 73 further comprising the step of adding a compatibilizing amount of thermoplastic effective for facilitating the dispersion of said masterbatch formulation in a thermoplastic to be rendered flame retardant.

76. A process as in claim 75 wherein said thermoplastic is selected from the group consisting of polypropylene, polyethylene, polycarbonate, polystyrene, acrylonitrile-butadiene-styrene terpolymer, polyphenylene oxide-polystyrene blends, acrylic polymer, polyurethane and polyamide.

77. A process as in claim 73 wherein said silicone is an organopolysiloxane comprised of chemically combined siloxy units selected from the group consisting of $R_3SiO_{0.5}$, $R_2SiO$, $RSiO_{1.5}$, $R^1R_2SiO_{0.5}$, $RR^1SiO$, $(R^1)_2SiO$, $R^1SiO_{1.5}$ and $SiO_2$ units and mixtures thereof wherein each R represents independently a saturated or unsaturated monovalent hydrocarbon radical, $R^1$ represents independently a saturated or unsaturated monovalent hydrocarbon radical or a radical selected from the group consisting of a hydrogen atom, hydroxyl, alkoxyl, aryl, vinyl, or allyl radicals and wherein said organopolysiloxane has a viscosity of approximately 600 to 300,000,000 centipoise at 25° C.

78. A process as in claim 77 wherein said silicone is an essentially linear polydimethylsiloxane copolymers having a viscosity of 90,000 to 150,000 at 25° C.

79. A process as in claim 73 wherein said Group IIA metal organic salt is a Group IIA metal carboxylic acid salt containing at least 6 carbon atoms.

80. A process as in claim 73 wherein said Group IIA metal is selected from the group consisting of magnesium, calcium, barium and strontium.

81. A process as in claim 73 wherein said carboxylic acid salt is selected from the group consisting of stearates, oleates, palmitates, myristates, laurates, undecylenates, 2-ethylhexanoates and hexanoates.

82. A process as in claim 73 wherein said silicone resin is present in an amount of 1 to 10 percent by weight and is comprised essentially of polytrimethylsilyl silicate having a ratio of approximately 0.6 to 2 M units per Q unit.

83. A process as in claim 73 further comprising the step of adding, approximately, 1 to 20 percent by weight of the total composition of an organic halide.

84. A process as in claim 83 wherein said organic halide is decabromodiphenyl oxide.

85. A process as in claim 73 further comprising the step of adding aluminum trihydrate in an amount of, approximately, 5 to 80 percent by weight of the total composition.

86. A process as in claim 73 further comprising the step of adding antimony oxide in an amount of, approximately, 1 to 10 percent by weight of the total composition.

87. A process as in claim 73 further comprising the step of adding a filler selected from the group consisting of talc, wollastonite, and calcium carbonate.

88. A process as in claim 73 further comprising the step of adding an amount of catalyst effective for curing said composition thereby providing a flame retardant article.

89. A process as in claim 73 further comprising the step of heat molding the thermoplastic.

* * * * *